(12) United States Patent
Schwarz

(10) Patent No.: US 10,675,010 B2
(45) Date of Patent: Jun. 9, 2020

(54) DEVICE FOR FIRMLY CLAMPING A MEDICAL GUIDE WIRE

(71) Applicant: Urotech GmbH, Rohrdorf-Achenmuehle (DE)

(72) Inventor: Werner Schwarz, Ruhpolding (DE)

(73) Assignee: Urotech GmbH, Rohrdorf-Achenmuehle (DE)

( * ) Notice: Subject to any disclaimer, the term of this patent is extended or adjusted under 35 U.S.C. 154(b) by 343 days.

(21) Appl. No.: 15/544,966

(22) PCT Filed: Jan. 20, 2016

(86) PCT No.: PCT/DE2016/000020
§ 371 (c)(1),
(2) Date: Jul. 20, 2017

(87) PCT Pub. No.: WO2016/116093
PCT Pub. Date: Jul. 28, 2016

(65) Prior Publication Data
US 2018/0271504 A1  Sep. 27, 2018

(30) Foreign Application Priority Data
Jan. 21, 2015  (DE) .................... 20 2015 000 456 U

(51) Int. Cl.
*A61B 17/00* (2006.01)
*A61B 90/30* (2016.01)
(Continued)

(52) U.S. Cl.
CPC .............. *A61B 17/00* (2013.01); *A61B 90/30* (2016.02); *A61L 31/04* (2013.01); *A61L 31/14* (2013.01);
(Continued)

(58) Field of Classification Search
CPC .................... A61B 17/00; A61B 90/30; A61B 2017/00862; A61B 2017/00907;
(Continued)

(56) References Cited

U.S. PATENT DOCUMENTS 4,726,369 A    2/1988  Mar
5,219,332 A  * 6/1993  Nelson .................... A61B 17/22
                                                              600/434

(Continued)

FOREIGN PATENT DOCUMENTS

DE    10 2004 017 734 B4   10/2007
DE    10 2012 104 961 A1   12/2013
(Continued)

OTHER PUBLICATIONS

International Search Report of PCT/DE2016/000020, dated May 30, 2016.

*Primary Examiner* — Jacqueline Cheng
*Assistant Examiner* — Tho Q Tran
(74) *Attorney, Agent, or Firm* — Collard & Roe, P.C.

(57) ABSTRACT

For the purpose of firmly clamping a medical guide wire which can be rotated and displaced in a longitudinal opening of an accommodating body, a clamping mechanism is present either just at one end of the longitudinal opening or at each end of the longitudinal opening, the clamping mechanism having a widened opening region, which runs transversely to the longitudinal opening, and a clamping-member arrangement, which is connected to the accommodating body in an elastically flexible manner and has an edge part, which is located in the opening region and against which the guide wire, once pivoted out of the longitudinal opening, can be brought into abutment at the relevant end of the accommodating body and at the clamping-member arrangement, (Continued)

Figure 1:
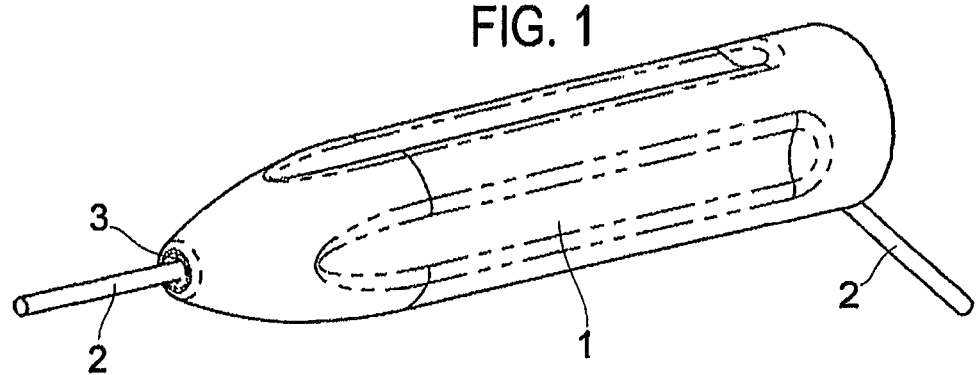

with the capability of the guide wire to be displaced and/or rotated being blocked in the process.

10 Claims, 4 Drawing Sheets

(51) Int. Cl.
    *A61L 31/14*     (2006.01)
    *A61M 25/09*     (2006.01)
    *A61L 31/04*     (2006.01)

(52) U.S. Cl.
    CPC ............... *A61M 25/09041* (2013.01); *A61B 2017/00469* (2013.01); *A61B 2017/00862* (2013.01); *A61B 2017/00907* (2013.01); *A61B 2090/309* (2016.02); *A61M 2025/09116* (2013.01); *A61M 2025/09125* (2013.01); *A61M 2205/587* (2013.01)

(58) Field of Classification Search
    CPC .... A61B 2090/309; A61B 2017/00469; A61L 31/04; A61L 31/14; A61M 25/09041; A61M 2205/587; A61M 2025/09125; A61M 2025/09116
    See application file for complete search history.

(56) References Cited

U.S. PATENT DOCUMENTS

| | | | |
|---|---|---|---|
| 5,325,868 A * | 7/1994 | Kimmelstiel | A61B 17/22 |
| | | | 600/585 |
| 6,030,349 A | 2/2000 | Wilson et al. | |
| 6,033,414 A | 3/2000 | Tockman et al. | |
| 6,190,333 B1 * | 2/2001 | Valencia | A61M 25/09041 |
| | | | 600/585 |
| 7,076,285 B2 * | 7/2006 | Windheuser | A61M 25/0097 |
| | | | 600/434 |
| 2005/0240120 A1 | 10/2005 | Modesitt | |
| 2007/0219467 A1 * | 9/2007 | Clark | A61M 25/0113 |
| | | | 600/585 |

FOREIGN PATENT DOCUMENTS

| | | |
|---|---|---|
| WO | 2006/124580 A1 | 11/2006 |
| WO | 2013/052906 A2 | 4/2013 |

\* cited by examiner

Section I-I

Section II-II

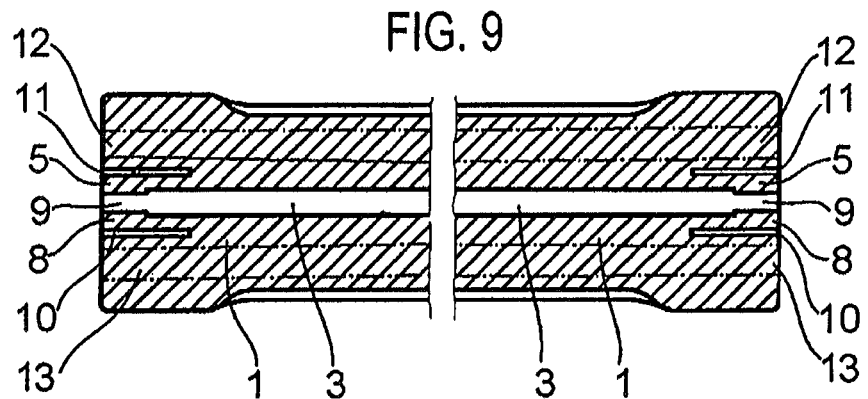
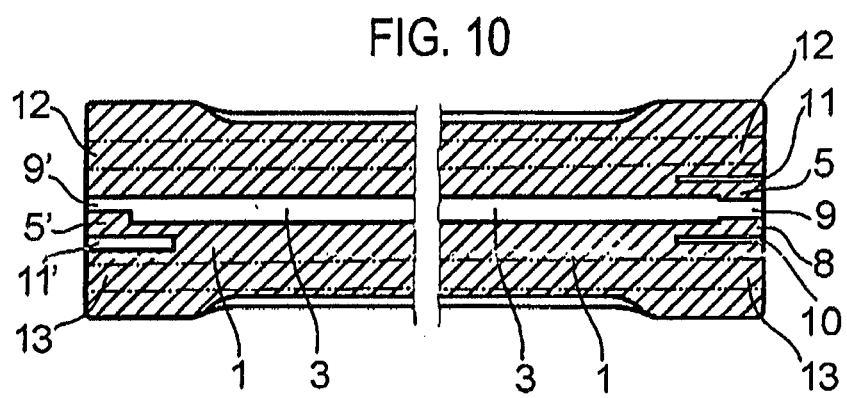
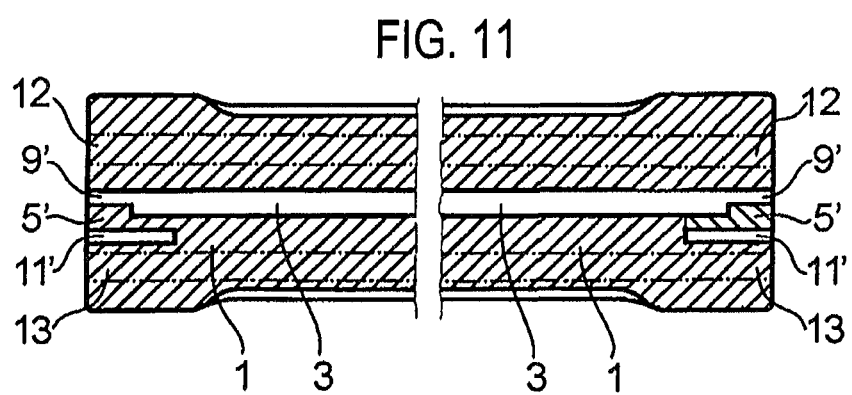

DEVICE FOR FIRMLY CLAMPING A MEDICAL GUIDE WIRE

CROSS-REFERENCE TO RELATED APPLICATIONS

This application is the National Stage of PCT/DE2016/000020 filed on Jan. 20, 2016, which claims priority under 35 U.S.C. § 119 of German Application No. 20 2015 000 456.3 filed on Jan. 21, 2015, the disclosures of which are incorporated by reference. The international application under PCT article 21(2) was not published in English.

The invention relates to an apparatus for firmly clamping a medical guide wire, comprising an accommodating body having a longitudinal opening that passes through it for accommodating the guide wire, which wire can be displaced and rotated in the longitudinal opening, and a clamping mechanism by means of which, when it becomes active, the displaceability and/or rotatability of the guide wire, which is accommodated in the said longitudinal opening, can be blocked.

Apparatuses of the above type are already known; they are also referred to as torquers. In the case of such a known torquer (U.S. Pat. No. 5,325,868), the longitudinal opening of the accommodating body is provided with gripper elements that lie opposite one another, between which a guide wire can be firmly clamped. Some of the gripper elements are disposed in stationary manner, and the other gripper elements are movable and are pressed against the gripper elements that are disposed in stationary manner by means of pressure springs. These gripper elements can be released from the gripper elements that are disposed in stationary manner, in single-handed operation, by means of a button that is connected with the movable gripper elements, in such a manner that a guide wire can be passed through between the gripper elements in question. If the button is subsequently released again, the guide wire is firmly clamped by the gripper elements. Although secure firm clamping of the guide wire is made possible in this way, occasionally the desire exists to achieve such firm clamping of a guide wire with less design effort.

In the case of another known torquer (U.S. Pat. No. 6,030,349), the longitudinal opening of the accommodating body is formed by a longitudinal slit that is open on the side, and the clamping mechanism is formed by a button part that also has a longitudinal slit that is open on the side. This button part is held in such a position, by means of elastomer bodies, so that its longitudinal slit and the longitudinal slit of the accommodating body are offset relative to one another. If, however, the button part is pressed into the accommodating body, the two longitudinal slits that are open on the side align with one another in such a manner that a medical guide wire can be accommodated by them. After the button part is released, the guide wire in question is then firmly clamped in the two longitudinal slits. Although secure, firm clamping of the guide wire is also made possible in this way, the desire also exists, in view of this torquer, to achieve firm clamping of a guide wire with less design effort.

In the case of another known torquer (DE 10 2004 017 734 B4), which also allows single-handed operation, the accommodating body consists of two sections that can pivot about a longitudinal axis, which sections are opened on the side in order to introduce a guide wire. Once the guide wire has been laid into these sections, they are compressed, thereby restricting the movement of the guide wire. In addition, this known torquer also has a clamping means in the form of a clamping lever disposed on one of the said sections so as to pivot counter to a reset force, which lever interacts with a counter-bearing provided on the other section, in the closed position. Although secure, firm clamping of a guide wire is made possible in this way, as well, here, too, the desire exists to achieve firm clamping of a guide wire with less design effort.

Finally, an apparatus for activation of a medical guide wire or transport wire is also already known (DE 10 2012 104 961 A1), comprising a housing having a passage for accommodating the guide wire or transport wire and at least one holding element, which is configured so that it can be activated by an external force or so that it is self-locking, at least in certain sections, in such a manner that a force-fit connection between the holding element and the guide wire or transport wire can be produced. In this known apparatus, at least one detection device for detection of forces and/or moments is provided, which forces act on the guide wire or transport wire when it is activated. Furthermore, at least one feedback device is provided, which is coupled or can be coupled with the detection device, to give off at least one signal. By means of providing the detection device, data can be obtained using the aforementioned forces and/or moments, and conclusions can be drawn with regard to stress on the hollow-wall blood vessel walls in the region of which the guide wire or transport wire in question is being used. In view of the design effort required for secure, firm clamping of a guide wire or transport wire, however, here, too, the desire exists to achieve firm clamping of a guide wire with less design effort.

The present invention is therefore based on the task of showing a way how it is possible to make do, in the case of an apparatus of the type stated initially, with less design effort than in the case of the previously known apparatuses for firmly clamping a medical guide wire, which is resilient because of its inherent elasticity.

The task indicated above is accomplished according to the invention, in the case of an apparatus of the type stated initially, in that the clamping mechanism is formed either only at one end of the longitudinal opening of the accommodating body or at each end of the longitudinal opening of the accommodating body, that the respective clamping mechanism, at its related end of the accommodating body, has a widened opening region, which runs transversely to the longitudinal opening of the accommodating body and extends toward the longitudinal opening over a distance that is shorter than the longitudinal opening is long, and has a clamping member arrangement, and that the respective clamping member arrangement is connected with the accommodating body in an elastically bendable manner, between its widened opening region and the said longitudinal opening, extends parallel to the longitudinal opening over a distance that is shorter than the said distance is long in the direction of the longitudinal opening, and has an edge part that faces the related opening region, on its side that faces away from the end in question and lies in the opening region, on which part the guide wire can be brought into contact after it has been pivoted out of the longitudinal opening at the related end of the accommodating body, and past the clamping member arrangement, into the opening region that is present at this end of the accommodating body, blocking its displaceability and/or rotatability.

The invention is characterized by the advantage of a particularly low design effort, in order to securely and firmly clamp a medical guide wire that is resilient as the result of its inherent elasticity. The design configuration of the apparatus that is decisive for such firm clamping, according to the invention, merely comprises widening of the said longitudinal opening to form an opening region, in which the clamping member arrangement is situated with an edge part against which the guide wire lies after it has been pivoted out of the said longitudinal opening into the opening region, and is thereby securely and firmly held. The related design effort is clearly less than that in the case of the known apparatuses or torquers considered initially. Furthermore, the apparatus according to the invention is characterized in that it allows easy single-handed operation, by means of which a guide wire can not only be firmly clamped in the apparatus in question but also can be released from its firm clamping again, so that it can be displaced in the apparatus without hindrance.

Preferably, the respective opening region runs at an angle between 10° and 120° with reference to the longitudinal opening of the accommodating body. Such an angle arrangement has proven to be particularly advantageous for the firm clamping of a guide wire that is being aimed at.

According to a practical further development of the invention, the respective clamping member arrangement is formed between the longitudinal opening and the opening region, by means of a single clamping element that is provided with an interstice toward an edge region of the longitudinal opening, and the interstice has a spacing that allows pressing the guide wire through, out of the longitudinal opening into the said opening region, and from the latter into the longitudinal opening. In this way, the advantage of a particularly low design effort for firmly clamping a guide wire is obtained.

According to another practical further development of the invention, the respective clamping member arrangement is formed by means of two clamping elements between the longitudinal opening and its related opening region, which elements are provided leaving an interstice between them, at diametrically opposite locations, in each instance, of connection regions between the longitudinal opening and the opening region in question, and the interstice has a distance that allows the guide wire to be pressed through from the longitudinal opening into the said opening region and from the latter into the longitudinal opening. In this way, the advantage of a particularly low design effort for firmly clamping a guide wire is obtained.

It is practical if the respective clamping element has a slanted chamfer on its side facing the longitudinal opening. In this way, the guide wire can be pivoted out of the said longitudinal opening of the accommodating body into the related opening region in particularly easy manner.

Preferably, the respective clamping element is formed on the accommodating body in the connection region between the related longitudinal opening and its related opening region. This brings with it the advantage that the accommodating body, including the respective clamping element, can be produced in one molding procedure such as an injection-molding procedure.

According to another practical embodiment of the invention, the respective clamping element consists of a material that is different from the material of the accommodating body, and is separately attached to the accommodating body in a connecting region between the longitudinal opening and its related opening region. In this way, the advantage is obtained that the respective clamping element can be produced from a material that is harder than the material of the accommodating body, for example. In this way, edges can be achieved on the respective clamping element, which are particularly effective for the firm clamping of the guide wire that is being aimed at. The said attachment of the respective clamping element to the connection region between the longitudinal opening and its related opening region can take place by means of an adhesive connection or by means of laser welding, for example.

Preferably, the apparatus according to the invention consists of plastic, particularly a biocompatible plastic. As a result, the apparatus in question can be used, without problems, in medical areas in which it can come into contact with bodies of individuals and, in particular, with their bodily fluids.

According to a further practical embodiment of the invention, the accommodating body is at lest partially phosphorescent or fluorescent on its outer surface. This makes it possible, in advantageous manner, to quickly find the apparatus according to the invention, together with the guide wire accommodated in it, after it has previously been irradiated with radiation suitable for development of the phosphorescence or fluorescence, in working spaces that are usually darkened, such as operating rooms.

Alternatively or in addition to the practical embodiment of the invention last being considered, the apparatus according to the invention contains at least one light source, particularly in an accommodating opening formed in the accommodating body, which consists of a translucent material. In this way, too, the advantage is obtained that the apparatus according to the invention, together with the guide wire accommodated in it, can be quickly found in working spaces that are usually darkened, such as operating rooms.

The invention will be explained in greater detail below, using some exemplary embodiments and using drawings.

Figure 2:
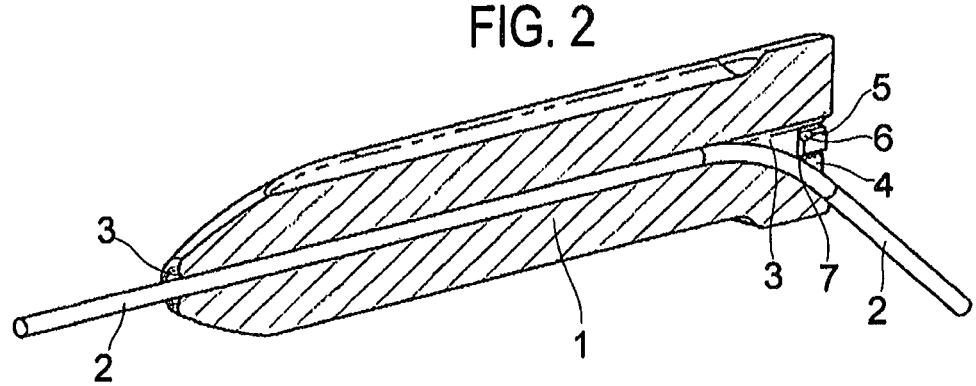
Figure 3:
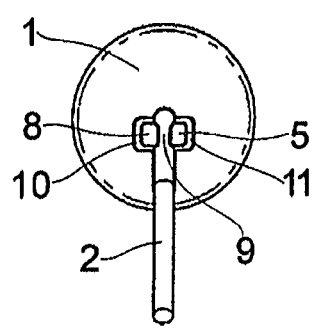
Figure 4:
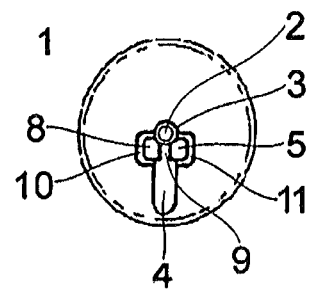
Figure 5:
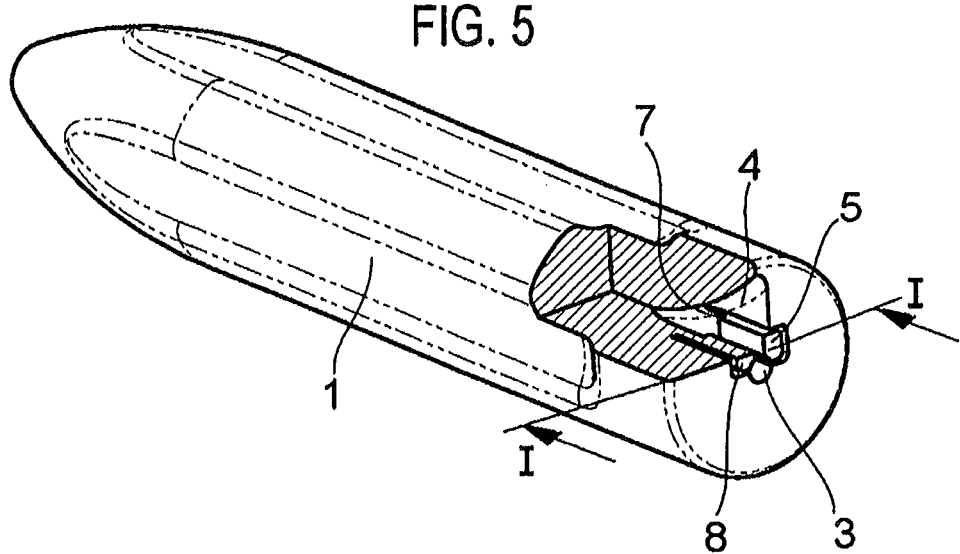
Figure 6:
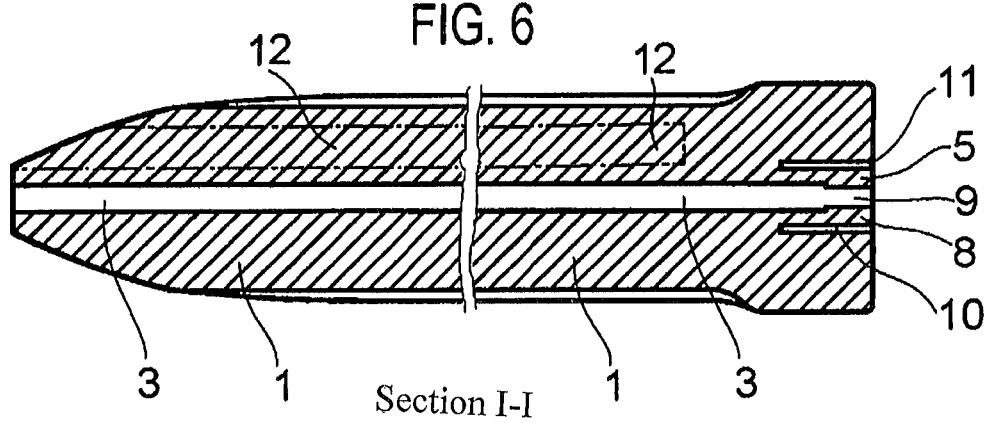
Figure 7:
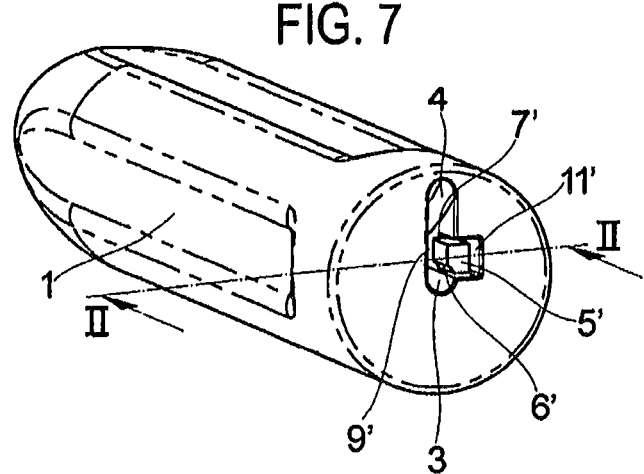
Figure 8:
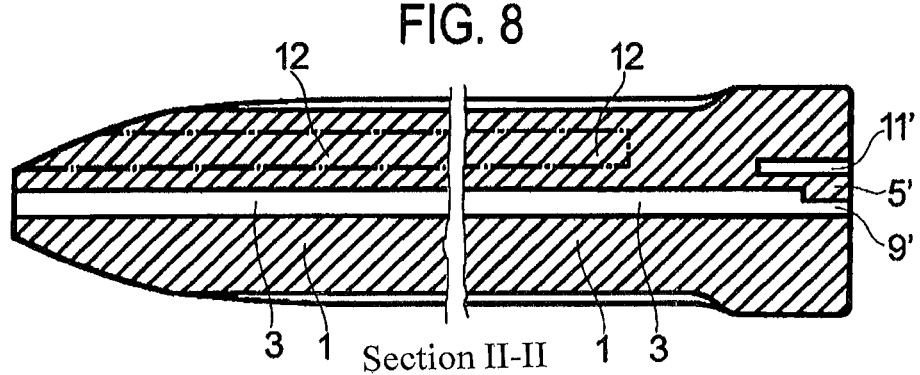

The drawings show:

FIG. 1 not to scale, a perspective view of a first exemplary embodiment of an apparatus according to the invention, with a guide wire, FIG. 2 a longitudinal-section view through the apparatus shown in FIG. 1, FIG. 3 a top view of the end of the apparatus in question, together with a guide wire, which end lies on the right side in FIG. 1, FIG. 4 the same top view as in FIG. 3, but without the guide wire, FIG. 5 the apparatus shown in FIG. 1 in a different perspective representation, also not to scale, and with a partial detail, FIG. 6 a sectional view of the apparatus shown in FIG. 5, along the section line I-I shown in that drawing, FIG. 7 in a similar perspective representation as that in FIG. 5, an apparatus according to a second exemplary embodiment of the invention, FIG. 8 not to scale, a sectional view of the apparatus shown in FIG. 7, along the section line II-II shown in that drawing, FIG. 9 not to scale, a sectional view of an apparatus according to a third exemplary embodiment of the invention, FIG. 10 not to scale, a sectional view of an apparatus according to a fourth exemplary embodiment of the invention, FIG. 11 not to scale, a sectional view of an apparatus according to a fifth exemplary embodiment of the invention.

Before the drawings are discussed in detail, it should be noted that in all the figures, devices or elements that are the same as or correspond to one another are referred to with the same reference symbol.

In FIG. 1, a perspective view of a first exemplary embodiment of an apparatus according to the invention is shown not to scale. Here, the apparatus in question has a cylindrical accommodating body 1 having a round or oval cross-section; the accommodating body 1 preferably consists of a biocompatible plastic, such as acrylonitrile butadiene styrene (ABS), in which a medical guide wire 2 is accommodated, specifically in a longitudinal opening 3 that passes through the accommodating body 1 in its longitudinal direction. In this regard, the diameter of the longitudinal opening 3 is so large that the guide wire 2 can be displaced in it so as to slide without hindrance in the longitudinal direction of the opening.

In practice, the guide wire can possess a diameter between 0.5 and 1 mm; it usually consists of a spring-elastic material such as stainless steel, and is provided with a plastic coating. The accommodating body 1 can possess an outside diameter of 10 mm, for example, and a length of a few centimeters, such as 5 cm, for example.

On its end that lies on the left in FIG. 1, which end is considered to be the distal end, the accommodating body 1 narrows conically from its outer surface toward its longitudinal opening 3. On its end that lies on the right in FIG. 1, which end is considered to be the proximal end, the accommodating body 1 has a planar surface from which the guide wire 2 is pivoted out of the longitudinal opening 3. By means of this pivoting out, the guide wire 2 is firmly clamped in the accommodating body 2, as will still become evident, in such a manner that it can no longer or no longer easily be rotated and/or displaced with reference to the accommodating body 1. Some grip recesses are provided around the cylindrical circumference region of the accommodating body 1, which facilitate grabbing and holding the accommodating body 1.

In FIG. 2, the apparatus shown in FIG. 1 is shown in a longitudinal-section view. In this sectional view, it can be seen at the right, proximal end of the accommodating body 1 that there, a widened opening region 4 runs transversely to the longitudinal opening 3 of the accommodating body 1, which region extends over a distance that is shorter than the longitudinal opening 3 is long. To state it differently, this means that the longitudinal opening 3 of the accommodating body 1 is provided with the widened opening region 4 at its proximal end. Here, this opening region 4 runs at an angle of about 45° with reference to the longitudinal opening 3 of the accommodating body 1. In general, however, this angle can amount to about 10° to 120° with reference to the longitudinal opening 3 of the accommodating body 1. At an angle that is greater than about 45°, the accommodating body 1 is then open on the side on which the guide wire 2 is pivoted out of it.

In the widened opening region 4 provided at the proximal end of the accommodating body 1, a block-shaped element is shown in FIG. 2, which represents a clamping element 5 for the guide wire 2. This clamping element 5 belonging to a clamping member arrangement, which will still be considered in greater detail below, is elastically connected with the accommodating body 1 so that it can be bent outward with its side that faces away from the proximal end of the accommodating body 1. This elastic bendability is utilized, according to the invention, to pivot the guide wire 2, which at first can be displaced without hindrance in the longitudinal opening 3, at the proximal end of the accommodating body 1, out of the longitudinal opening into the widened opening region 4. On its side that faces the longitudinal opening 3 of the accommodating body 1, the clamping element 5 has a slanted chamfer 6, the significance of which will still be discussed in greater detail below.

The aforementioned clamping element 5 extends parallel to the longitudinal opening 3 over a distance that is shorter than the aforementioned distance of the widened opening region 4 is long in the direction of the longitudinal opening 3. To state it more precisely, the clamping element 5 extends from the proximal end of the accommodating body 1 so far into this body that the guide wire 2, after having been pivoted out of the longitudinal opening 3, at the end in question, into the widened opening region 4, is able to make contact between a side facing the proximal end of the accommodating body 1 and an edge part 7 of the clamping element 5, which the clamping element 5 has between its side that lies facing away from the proximal end in question, lying in the widened opening region 4, and its side that faces away from the longitudinal opening 3.

At this edge part 7 of the clamping element 5, the guide wire 2, after having been pivoted out of the longitudinal opening 3 at the proximal end of the accommodating body 1 and past the clamping element 4 of the clamping member arrangement, can be introduced into the aforementioned widened opening region 4, and, because of its contact with the said edge part 7, it is blocked with regard to its rotatability and its displaceability, at least in the direction toward the proximal end of the accommodating body 1. In this regard, the slanted chamfer 6 provided on the clamping element 5 facilitates pivoting of the guide wire 2 out of the longitudinal opening 3 of the accommodating body 1. If the blocking of the guide wire 2 as described is supposed to be canceled out again, then the wire is pivoted back toward the longitudinal opening 3 at the proximal end of the accommodating body 1.

In FIGS. 3 and 4, top views of the proximal end of the accommodating body 1 and thereby of the apparatus shown in FIG. 1 as a whole are shown. In this regard, FIG. 3 shows the top view with the guide wire 2 situated in its clamping position, and FIG. 4 shows the top view of the guide wire 2 released from its clamping position. In both top view, aside from the clamping element 5, a further clamping element 8 can be seen, which, together with the clamping element 5, forms the aforementioned clamping member arrangement. The clamping element 8 is positioned in the accommodating body 1 diametrically opposite the clamping element 5, at a certain distance from it—in other words with an interstice 9 from it. For the remainder, the clamping element 8 is structured in the same manner as the clamping element 5, in other words also with a slanted chamfer corresponding to the slanted chamfer 6, and with an edge part corresponding to the edge part 7. The two clamping elements 5 and 8 are formed here as projecting elements in the accommodating body 1, together with it. However, it is also possible to provide the two clamping elements 5 and 8 as separate elements, composed of a different, preferably biocompatible material, for example from polyoxymethylene (POM), than the material of which the accommodating body 1 consists. These separate clamping elements must be connected with the accommodating body 1 at the locations at which the clamping elements 5 and 8 are provided according to FIGS. 5 and 6, for example by means of gluing or welding.

The clamping member arrangement mentioned above, having the two clamping elements 5 and 8, blocks the guide wire 2, according to FIG. 3, after it has been pivoted out of the longitudinal opening 3 at the proximal end of the accommodating body 1, in terms of its rotatability and its displaceability, at least in the direction toward the proximal end of the accommodating body 1. After it has been pivoted back into the longitudinal opening 3 according to FIG. 4, blocking of the guide wire 2 is canceled out again. The clamping element 8 is positioned in the accommodating body 1 diametrically opposite the clamping element 5, at a certain distance from it—in other words with an interstice 9 from it. On its sides that face away from the aforementioned interstice 9, interstices 10 and 11 are provided between the two clamping elements 5 and 8 and inner wall regions of the accommodating body 1. In this regard, the length dimensions of the interstices 10 and 11 in the longitudinal direction of the accommodating body 1 are greater than the length of each of the clamping elements 5 and 8 in the longitudinal direction in question. Preferably, the length dimensions of the interstices 10 and 11 in the longitudinal direction of the accommodating body 1 are at least about twice as great as the length of each of the clamping elements 5 and 8 as just mentioned.

In FIG. 5 and FIG. 6, the relationships explained above, at the proximal end of the accommodating body 1, are specified in even greater detail. In this regard, FIG. 5 shows the apparatus shown in FIG. 1, in a different perspective representation, also not to scale, but with a partial detail, and FIG. 6 shows a sectional view of the apparatus shown in FIG. 5, along the section line I-I shown there. From the two FIGS. 5 and 6 it is evident, in greater detail, how the clamping member arrangement with the two clamping elements 5 and 8 is configured at the proximal end of the accommodating body 1. In this regard, it is particularly evident from FIG. 6 that the two clamping elements 5 and 8 have overhangs that run toward the longitudinal center of the accommodating body. The dimensions of these overhangs in the direction toward the longitudinal center of the accommodating body 1 correspond, in each instance, to the dimension of the interstices 10 and 11 in the diametrical transverse direction of the accommodating body 1; they are preferably at least equal to the related transverse dimensions of these interstices 10 and 11 in the diametrical transverse direction, in other words the dimensions that are present in the top views according to FIGS. 3 and 4 and in the sectional view according to FIG. 6, in the diametrical transverse direction of the accommodating body 1.

The dimensions of the interstices 9, 10, and 11 are therefore selected in such a manner that the two clamping elements 5 and 8 are accommodated in the interstices 10 and 11, respectively, when the guide wire 2 is pivoted between its clamped position and its non-clamped position, with their sides facing away from the interstice 9, and that the guide wire 2 can be pivoted through the interstice 9 without problems.

In addition, in FIG. 6 a region marked with dot-dash lines is also indicated in FIG. 6, within the accommodating body 1, which region is supposed to represent an accommodating opening 12, the significance of which will still be discussed in greater detail below. This accommodating opening 12 extends, here, from the distal end of the accommodating body 1 only over a part of the total length of the accommodating body 1; however, it can be provided in the accommodating body 1 transversely to its longitudinal direction.

While above, a first exemplary embodiment of the apparatus according to the invention was described using FIGS. 1 to 6, in which the clamping member arrangement contains two clamping elements, namely the clamping elements 5 and 8, FIG. 7 and FIG. 8 show an apparatus according to a second exemplary embodiment of the invention, in which the clamping member arrangement contains only one clamping element 5'. In this regard, FIG. 7 shows this apparatus according to the second exemplary embodiment of the invention in a similar perspective representation as FIG. 5, and FIG. 8 shows a sectional view of the apparatus shown in FIG. 7, not to scale, along the section line II-II in that drawing. The accommodating body 1 shown in FIGS. 7 and 8 is also configured to be cylindrical, and it also has a round or oval cross-section.

The clamping element 5' provided in the apparatus shown in FIGS. 7 and 8 corresponds, to a great extent, to the clamping element 5 in the apparatus according to the first exemplary embodiment of the invention. The clamping element 5' accordingly has a slanted chamfer 6' and an edge part 7'. However, here the overhang of the clamping element 5' in the direction transverse to the longitudinal center of the accommodating body 1 is greater than and preferably twice as great as that of the clamping element 5. Furthermore, here only two interstices 9' and 11' are provided.

The dimension of the overhang of the clamping element 5' in the direction toward the longitudinal center of the accommodating body 1 corresponds to the dimension of the interstice 11' in the diametrical transverse direction of the accommodating body 1; it is preferably at least equal to the related transverse dimension of this interstice 11' in the diametrical transverse direction, in other words the dimension that is present according to FIG. 8 in the diametrical transverse direction of the accommodating body 1.

In this regard, the length dimension of the interstice 11' in the longitudinal direction of the accommodating body 1 is greater than the length of the clamping element 5' in the longitudinal direction in question. Preferably, the length dimension of the interstice 11' in the longitudinal direction of the accommodating body 1 is at least twice as great as the length of the clamping element 5' as just mentioned.

The dimension of the interstice 9', together with the dimensions of the interstice 11', is selected in such a manner that the single clamping element 5' is accommodated in the interstice 11' when the guide wire 2 is pivoted between its clamped position and its non-clamped position, with its side facing away from the interstice 9', and that the guide wire 2 can be pivoted through the interstice 9' without problems.

In FIG. 8, a region also marked with dot-dash lines is indicated within the accommodating body 1, which region is supposed to represent an accommodating opening 12, the significance of which will still be discussed in greater detail below. This accommodating opening 12 extends, here, too, from the distal end of the accommodating body 1 only over a part of the total length of the accommodating body 1; however, here too it can be provided in the accommodating body 1 transversely to its longitudinal direction.

Above, two exemplary embodiments of the apparatus according to the invention have been described, in which the clamping member arrangement is provided only at the proximal end of the accommodating body 1 and thereby of the entire apparatus. In FIGS. 9 to 11, three further exemplary embodiments of the apparatus according to the invention are shown, in which clamping member arrangements are provided not only at the proximal end but also at the distal end of the accommodating body 1 and thereby of the entire apparatus. By means of these clamping member arrangements, the clamping effect on the guide wire 2 in the respective accommodating body 1 can be further increased, so that it cannot be pulled out of the accommodating body 1, neither at its distal end nor at its proximal end. All the apparatuses according to FIGS. 9, 10, and 11 also have a cylindrical accommodating body 1 having a round or oval cross-section.

Thus, FIG. 9 shows a sectional view, not to scale, of an apparatus according to a third exemplary embodiment of the invention, in which two clamping member arrangements are present, as they can be seen in the sectional view according to FIG. 6. FIG. 10 shows a sectional view, not to scale, of an apparatus according to a fourth exemplary embodiment of the invention, in which two different clamping member arrangements are provided, namely a clamping member arrangement as it can be seen in the sectional view according to FIG. 6, and a clamping member arrangement as it can be seen in the sectional view according to FIG. 8. FIG. 11, finally, shows a sectional view, not to scale, of an apparatus according to a fifth exemplary embodiment of the invention, in which two clamping member arrangements are present, as they can be seen in the sectional view according to FIG. 8. For all these clamping member arrangements, what has been said above with regard to the clamping member arrangements described using FIGS. 1 to 8 applies.

In the sectional views according to FIG. 9, FIG. 10, and FIG. 11, regions marked by dot-dash lines, which are supposed to represent accommodating openings 12, 13, are indicated, in each instance. These accommodating openings 12, 13, in contrast to the accommodating openings 12 according to FIG. 6 and FIG. 8, here run between the distal end and the proximal end of the respective accommodating body 1, in each instance, in other words in its longitudinal direction. However, the openings in question can also be contained in the accommodating body 1 transversely to its longitudinal direction, in each instance. In all these accommodating openings, in other words not only according to FIGS. 9 to 11, but also according to FIGS. 6 and 8, a light source can be accommodated, which can comprise one or more light-emitting diodes (LEDs) together with the related power source (batteries, for example). In this regard, the accommodating body 1 can consist of a translucent material, so that the light emitted from the light source in question can penetrate the accommodating body 1 and reach its outer side. However, it is also possible to dispose the light source in question on the outer side of the accommodating body 1, in order to emit light. As was mentioned initially, such light emission can be very helpful for the person working with an apparatus according to the invention, such as a surgeon, in order to be able to quickly find this apparatus again after its use in working spaces that are usually darkened, such as operating rooms.

Alternatively or in addition to the measure explained above, of providing a light source in and/or on the accommodating body 1, the accommodating body 1 can be configured to be at least partially phosphorescent or fluorescent on its outer surface, according to the invention. In this way, an apparatus according to the invention, after having been irradiated with radiation suitable for developing the phosphorescence or fluorescence, can quickly be located again and therefore grasped in working spaces in which work is done with such an apparatus and the guide wire accommodated in it, which spaces are usually darkened, such as operating rooms.

As was mentioned in connection with FIG. 1, the apparatus according to the invention shown there as a first exemplary embodiment contains a cylindrical accommodating body 1, which preferably consists of a biocompatible material such as acrylonitrile butadiene styrene (ABS). This material selection also applies for the apparatuses according to the other exemplary embodiments explained above. The method of procedure mentioned in connection with the first exemplary embodiment, namely that of providing each of the clamping elements 5 and 8 formed together with the accommodating body 1 as a separate clamping element and connecting it with the accommodating body, can also be applied accordingly in all the other exemplary embodiments that were explained. In this regard, each such separate clamping element can consist of a different, preferably biocompatible material, such as of polyoxymethylene (POM), for example, than the material of which the related accommodating body 1 consists.

REFERENCE SYMBOL LIST 1 accommodating body
2 guide wire
3 longitudinal opening
4 opening region
5 clamping element
5' clamping element
6 slanted chamfer
6' slanted chamfer
7 edge part
7' edge part
8 clamping element
9 interstice
9' interstice
10 interstice
11 interstice
11' interstice
12 accommodating opening
13 accommodating opening

The invention claimed is:

1. Apparatus for clamping a medical guide wire (2), comprising:
an accommodating body (1) having a longitudinal opening (3) that passes through the accommodating body for accommodating the medical guide wire (2), the medical guide wire capable of being displaced and rotated in the longitudinal opening (3), and a clamping mechanism that when active, the displaceability and/or rotatability of the medical guide wire (2), which is accommodated in the longitudinal opening (3), is blocked;
wherein the clamping mechanism is formed either only at one end of the longitudinal opening (3) of the accommodating body (1) or at each end of the longitudinal opening (3) of the accommodating body (1);
wherein the damping mechanism has a widened opening region (4), which extends toward the longitudinal opening (3) over a distance that is shorter than the longitudinal opening (3) is long, and has a clamping member arrangement, (5, 8; 5');
wherein the clamping member arrangement is connected with the accommodating body (1) in an elastically bendable manner, between the widened opening region (4) and the longitudinal opening (3), extends parallel to the longitudinal opening (3) over a distance that is shorter than a length of the longitudinal opening (3), and has an edge part (7;7') that faces the widened opening region (4), on a side that faces away from the end and lies in the widened opening region (4), on which part the guide wire (2) can be brought into contact after the guide wire has been pivoted out of the longitudinal opening (3), and past the clamping member arrangement, into the opening region (4), blocking displaceability and/or rotatability of the accommodating body.

2. Apparatus according to claim 1, wherein the widened opening region (4) runs at an angle between 10° and 120° with reference to the longitudinal opening of the accommodating body.

3. Apparatus according to claim 1, wherein the clamping member arrangement (5') is formed between the longitudinal opening (3) and the widened opening region (4), by means of a single clamping element (5') that is provided with an interstice (9') toward an edge region of the longitudinal opening (3), and wherein the interstice (9') has a spacing that allows pressing the guide wire (2) through, out of the longitudinal opening (3) into the widened opening region (4), and from the widened opening region into the longitudinal opening (3).

4. Apparatus according to claim 1, wherein the clamping member arrangement (5, 8) is formed by means of two clamping elements (5, 8) between the longitudinal opening (3) and the widened opening region (4), wherein the two clamping elements are provided leaving an interstice (9) between them, at diametrically opposite locations, in each instance, of connection regions between the longitudinal opening (3) and the opening region (4), and wherein the interstice (9) has a distance that allows the guide wire (2) to be pressed through from the longitudinal opening (3) into the said widened opening region (4) and from the widened opening region into the longitudinal opening (3).

5. Apparatus according to claim 3, wherein the clamping element (5') has a slanted chamfer (6') on a side facing the longitudinal opening (3).

6. Apparatus according to claim 4, wherein the clamping elements (5,8) is formed on the accommodating body (1) in a connection region between the longitudinal opening (3) and the widened opening region (4).

7. Apparatus according to claim 4, wherein the clamping elements (5,8) consists of a material that is different from the material of the accommodating body (1), and is separately attached to the accommodating body (1) in a connecting region between the longitudinal opening (3) and its widened opening region (4).

8. Apparatus according to claim 1, wherein the accommodating body is made of a plastic material.

9. Apparatus according to claim 1, wherein the accommodating body (1) is configured to be at least partially phosphorescent or fluorescent on an outer surface.

10. Apparatus according to claim 1, further comprising at least one light source, disposed in an accommodating opening (12; 13) that is formed in the accommodating body (1), and wherein the accommodating body consists of a translucent material.

* * * * *